(12) United States Patent
Baechler et al.

(10) Patent No.: US 9,275,013 B2
(45) Date of Patent: Mar. 1, 2016

(54) SYSTEM AND METHOD FOR ANALYSIS AND RECONSTRUCTION OF VARIABLE PULSE-WIDTH SIGNALS HAVING LOW SAMPLING RATES

(71) Applicant: QUALCOMM Incorporated, San Diego, CA (US)

(72) Inventors: Gilles Baechler, Onnens FR (CH); Ali Hormati, Renens (CH)

(73) Assignee: QUALCOMM Incorporated, San Diego, CA (US)

(*) Notice: Subject to any disclaimer, the term of this patent is extended or adjusted under 35 U.S.C. 154(b) by 0 days.

(21) Appl. No.: 13/800,754

(22) Filed: Mar. 13, 2013

(65) Prior Publication Data

US 2013/0245471 A1      Sep. 19, 2013

Related U.S. Application Data

(60) Provisional application No. 61/611,739, filed on Mar. 16, 2012.

(51) Int. Cl.
*A61B 5/0402* (2006.01)
*G06F 17/14* (2006.01)
*A61B 5/00* (2006.01)
*A61B 5/04* (2006.01)

(52) U.S. Cl.
CPC ............ *G06F 17/141* (2013.01); *A61B 5/0006* (2013.01); *A61B 5/0402* (2013.01); *A61B 5/04012* (2013.01); *A61B 5/7257* (2013.01)

(58) Field of Classification Search
CPC ..... A61B 5/7235; A61B 5/7253; A61B 5/7257
USPC ......................................................... 600/509
See application file for complete search history.

(56) References Cited

U.S. PATENT DOCUMENTS

| | | | |
|---|---|---|---|
| 4,947,857 A * | 8/1990 | Albert et al. ................. | 600/509 |
| 5,609,158 A | 3/1997 | Chan | |
| 5,891,047 A | 4/1999 | Lander et al. | |
| 6,377,843 B1 | 4/2002 | Naydenov et al. | |
| 6,647,287 B1 | 11/2003 | Peel, III et al. | |
| 7,706,992 B2 | 4/2010 | Ricci et al. | |
| 2004/0210617 A1 | 10/2004 | Vetterli et al. | |
| 2009/0190689 A1 | 7/2009 | Blu et al. | |
| 2011/0225218 A1 | 9/2011 | Eldar et al. | |

OTHER PUBLICATIONS

Blu T et al., "Sparse Sampling of Signal Innovations [Theory, algorithms, and performance bounds]," IEEE Signal Processing Magazine, vol. 25, No. 2, (Mar. 1, 2008), pp. 31-40, XP011206128, IEEE Service Center, Piscataway, NJ, US, ISSN: 1053-5888.

(Continued)

*Primary Examiner* — Joseph Dietrich
(74) *Attorney, Agent, or Firm* — Knobbe, Martens, Olson & Bear LLP

(57) ABSTRACT

Systems and methods are described herein for applying a predefined functional shape to coefficients of a discrete Fourier transform of a waveform. The waveform may based, at least in part, on an electro-cardiogram (ECG). The predefined functional shape may be parabolic, and may be defined on a logarithmic scale. The application of a predefined functional shape may allow a more accurate reconstruction of a waveform to be generated at a lower sampling rate.

34 Claims, 11 Drawing Sheets

(56) References Cited

OTHER PUBLICATIONS

Hao et al., "Compression of ECG as a Signal with Finite Rate of Innovation", Proceedings of the 2005 IEEE Engineering in Medicine and Biology 27th Annual Conference, Shanghai, China, Sep. 1-4, 2005, pp. 7564-7567.
Marziliano, et al., "Sampling and Exact Reconstruction of Bandlimited Signals With Additive Shot Noise," IEEE Transactions on Information Theory, vol. 52, No. 5, May 2006, pp. 2230-2233.
Seelamantula et al., "A Generalized Sampling Method for Finite-Rate-of-Innovation-Signal Reconstruction", 2008, IEEE Signal Processing Letters, vol. 15, pp. 813-816.
Tur, et al., "Innovation Rate Sampling of Pulse Streams With Application to Ultrasound Imaging," IEEE Transactions on Signal Processing, vol. 59, No. 4, pp. 1827-1842, Apr. 2011.
Vetterli et al., "Sampling Signals With Finite Rate of Innovation", IEEE Transactions on Signal Processing, Jun. 2002, pp. 1417-1428, vol. 50, No. 6.
Baechler G., Anonymous: "Sensing ECG signals with Variable Pulse Width Finite Rate of Innovation," EPFL Infoscience record Feb. 26, 2014, 2 pages, XP055122033.
Baechler G., "Sensing ECG signals with Variable Pulse Width Finite Rate of Innovation," Master's Thesis, Communication Systems, Ecole Polytechnique Federale de Lausanne, Switzerland, Mar. 16, 2012, 99 pages, XP055120865.
Baechler G., et al., "Finite rate of innovation based modeling and compression of ECG signals," 2013 IEEE International Conference on Acoustics Speech and Signal Processing (ICASSP 2013), May 26-31, 2013, Vancouver, Canada, May 26, 2013, pp. 1252-1256, XP032508088.
Bloor D., et al., "Optical properties of Bis (p-Toluene Sulphonate) Diacetylene—II. Low-temperature spectra2)" Physica Status Solid, vol. 39, 1997, pp. 607-614, XP055122046.
Clifford G.D., et al., "Model-based filtering, compression and classification of the ECG," International Journal of Bioelectromagnetism, vol. 7 (1), 2005, pp. 158-161, XP055094653.
International Search Report and Written Opinion—PCT/US2013/031332—ISA/EPO—Aug. 22, 2014.
King F.W., "Efficient numerical approach to the evaluation of Kramers-Kronig transforms," Journal of The Optical Society of America B, vol. 19 (10), Oct. 2002, pp. 2427-2436, XP055122017.
Maggs J.E., et al., "Generality of deterministic chaos, exponential spectra, and Lorentzian pulses in magnetically confined plasmas," Physical Review Letters, vol. 107 (18), pp. 185003-1 to 185003-5, Oct. 2011, XP055121534.
Nair A., et al., "Multichannel ECG analysis using VPW-FRI," 10th International Conference on Sampling Theory and Applications (SampTA2013), Jul. 1-5, 2013, Bremen, Germany, Jul. 1, 2013, pp. 125-128, XP055120861.
Nait-Ali A., et al., "Compression of physiological signals," In: "Compression of Biomedical Images and Signals," 2008, pp. 129-153; ISTE and John Wiley & Sons, XP055121451.
Niranjan U.C., et al., "ECG component delineation by Prony's method," Signal Processing, vol. 31 (2), Mar. 1993, pp. 191-202, XP026671027.
Ouamri A., et al., "ECG Compression method using Lorentzian functions model," Digital Signal Processing, vol. 17 (1), Dec. 2, 2006, pp. 319-326, XP005724191.
Quick R.F., et al., "Extension of FRI for modeling of electrocardiogram signals," 34th Annual International Conference of the IEEE Engineering in Medicine and Biology Society, Aug. 28-Sep. 1, 2012, San Diego, CA, USA, Aug. 28, 2012, pp. 2909-2912, XP055053558.

* cited by examiner

SYSTEM AND METHOD FOR ANALYSIS AND RECONSTRUCTION OF VARIABLE PULSE-WIDTH SIGNALS HAVING LOW SAMPLING RATES

CROSS REFERENCE TO RELATED APPLICATIONS

This application claims priority under 35 U.S.C. Section 119(e) to U.S. Provisional Application No. 61/611,739, filed on Mar. 16, 2012, which application is hereby incorporated by reference in its entirety.

TECHNICAL FIELD

This disclosure relates to systems and methods for applying a predefined functional shape to coefficients of a discrete Fourier transform of a waveform.

DESCRIPTION OF THE RELATED TECHNOLOGY

Signal parameterization is widely used in signal processing, storage, transmission, and analysis. Perhaps the most common is the use of Nyquist rate sampling, where a continuous time domain signal is represented by a set of sampled signal values at discrete times. As long as the original continuous signal is band limited to at most half the sampling rate, the set of samples can be used to reconstruct the complete signal by using, for example, a sine interpolation algorithm. In this common example, the signal is represented by a set of discrete parameters, the sample values, which can be stored, transmitted, and used at any time to completely reconstruct the original signal.

More recently, some non-bandlimited signals of practical interest have been parameterized in other ways. Although these signals may contain frequency components that are arbitrarily large, they are modeled by characteristics that limit the "rate-of-innovation" per unit time so that the signal can be parameterized with a finite set of values from which the original signal can be reconstructed. The problem to be solved then is how to derive a suitable set of parameter values from the original signal and how to reverse the process to reconstruct the complete signal using only the derived parameters. The prior art of Finite Rate of Innovation (FRI) based signal analysis is one such method of analyzing signals and is described in the following references: [1] M. Vetterli, P. Marziliano, T. Blu, "Sampling Signals with Finite Rate of Innovation", *IEEE Transactions on Signal Procesing*, vol. 50, no. 6, pp. 1417-1428, June 2002; [2] T. Blu, P. L. Dragotti, M. Vetterli, P. Marziliano, and L Coulot, "Sparse Sampling of Signal Innovations: Theory, Algorithms, and Performance Bounds", *IEEE Signal Processing Magazine*, vol. 25, no. 2, pp. 31-40, March 2008; [3] Y. Hao, P. Marziliano, M. Vetterli, T. Blu, "Compression of ECG as a Signal with Finite Rate of Innovation", Proc. of the 2005 IEEE Engineering in Medicine and Biology 27th Annual Conference, Shanghai, China, Sep. 1-4, 2005, pp. 7564-7567; [4] Marziliano, M. Vetterli and T. Blu, "Sampling and Exact Reconstruction of Bandlimited Signals With Additive Shot Noise," *IEEE Transactions on Information Theory*, vol. 52, No. 5, pp. 2230-2233, May 2006. In this method, waveforms or derivatives of waveforms are analyzed to identify the locations and amplitudes of Dirac functions (essentially infinitely narrow pulses) which are used to define signal features or markers for the boundaries of signal segments within the pseudo-periods. The signals or signal segments may then be reconstructed using the appropriate wave shapes or splines. These models (which may be referred to as Dirac-FRI models) described in the prior art are limited to two parameters for pulse descriptions, an amplitude and a position within a period (for pseudo-periodic signals), and they are restricted to a single pulse shape for reconstruction. Thus these models are limited in their ability to parameterize signals containing pulses of varying widths.

SUMMARY

The systems, methods, and devices of the invention each have several aspects, no single one of which is solely responsible for its desirable attributes. Without limiting the scope of this invention as expressed by the claims which follow, some features will now be discussed briefly. After considering this discussion, and particularly after reading the section entitled "Detailed Description" one will understand how the features of this invention provide advantages that include models for defining and parameterizing signals or system responses containing pulses of varying width. The parameters may define the signal and therefore can be used as a compressed version of the original signal. Storage of the parameters as a compressed version of the signal requires less storage space, making storage of signals more memory efficient.

In one implementation, a computer implemented method of reconstructing a time domain waveform from a compressed original time domain waveform comprises receiving, by a processor, parameters defining a compressed form of the original time domain waveform, generating, with the processor, discrete Fourier transform (DFT) coefficients from the parameters, adjusting, with the processor, the amplitudes of at least some of the generated DFT coefficients to more closely fit the amplitudes of at least some of the generated DFT coefficients to a predefined functional shape, performing, with the processor, an inverse discrete Fourier transform (IDFT) on a set of DFT coefficients including the adjusted DFT coefficients to produce a reconstructed time domain waveform. In some implementations, the predefined functional shape is parabolic on a logarithmic scale. In some implementations, the waveform is based, at least on part, on an electro-cardiogram (ECG). In some implementations, the parameters are derived from time domain samples of an original signal, and the time domains samples may be spaced at less than 120 Hz.

In another aspect, an processing apparatus comprises a memory having stored therein parameters defining a compressed form of an original time domain waveform, a processor configured to retrieve parameters, generate discrete Fourier transform (DFT) coefficients from the parameters, and adjust the amplitudes of at least some of the generated DFT coefficients to more closely fit the amplitudes of the at least some of the generated DFT coefficients to a predefined functional shape. The processor is also configured toperform an inverse discrete Fourier transform (IDFT) on a set of DFT coefficients including the adjusted DFT coefficients to produce a reconstructed time domain waveform.

In another aspect, a non-transitory, computer readable medium is disclosed, which comprises instructions that when executed cause a processor to perform a method comprising receiving, in the processor, parameters defining a compressed form of an original time domain waveform, generating, with the processor, discrete Fourier transform (DFT) coefficients from the parameters, adjusting, with the processor, the amplitudes of at least some of the generated DFT coefficients to more closely fit the amplitudes of at least some of the generated DFT coefficients to a predefined functional shape, performing, with the processor, an inverse discrete Fourier transform (IDFT) on a set of DFT coefficients including the adjusted DFI coefficients to produce a reconstructed time domain waveform.

DETAILED DESCRIPTION

Figure 1A:
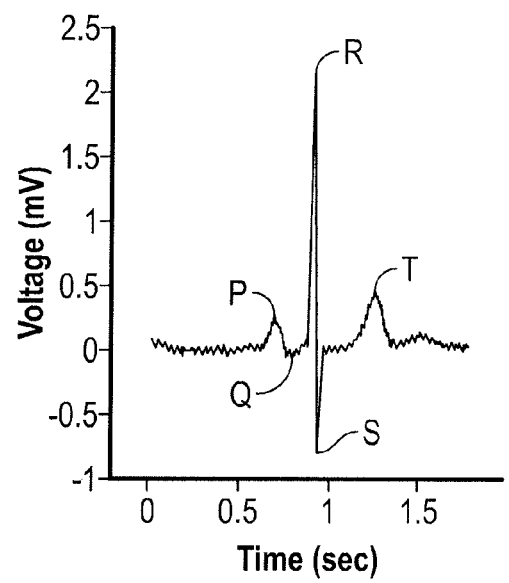
FIGS. 1A-1C illustrate reconstruction of an ECG waveform with a sum of Lorentzian pulses.

Various aspects of the novel systems, apparatuses, and methods are described more fully hereinafter with reference to the accompanying drawings. The teachings may be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the invention. For example, an apparatus may be implemented or a method may be practiced using any number of the aspects set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different systems, some of which are illustrated by way of example in the figures and in the following description of the preferred aspects. The detailed description and drawings are merely illustrative of the disclosure rather than limiting, the scope of the disclosure being defined by the appended claims and equivalents thereof.

The methods of the present disclosure may be applicable to a variety of systems. For example, the present disclosure may be particularly applicable to signal storage databases such as electro-cardiogram (ECG) databases. In one aspect, the methods herein may be used to parameterize ECG signals and then store those parameters in an ECG database. This may greatly reduce the cost and resources required for storing ECG signals as the memory allocation required to store the data is greatly reduced. Such ECG signal databases provide information used for evaluation and treatment of patients. Further, hospitals may require such ECG databases as part of storage of patient medical records. Thus, the systems and methods described herein may prove valuable to the medical field.

Many of the methods described herein overcome difficulties of the prior art by introducing parameters in the model which define the widths and asymmetries of the pulse shapes of the model and extends the mathematics and methodology of FRI analysis. Additionally, the disclosure defines the means for performing the analysis to estimate these parameters from the data. It generalizes the model of FRI to a four-parameter pulse model which can represent waveforms as the sum of overlapping pulses (defined by complex poles in the model), each of which is characterized by a position, symmetric component amplitude, asymmetric component amplitude, and width. The added degrees of freedom provided by this generalization greatly extend the range and class of signals that can be modeled and it permits the representation of overlapping of pulses rather than concatenations of waveform segments.

Signals that approximate the parameterization model described herein may be referred to as Variable Pulse-Width Finite Rate of Information (i.e. the VPW-FRI) signals. An example of this class of signals is the heart beat in an ECG waveform as illustrated in FIG. 1A. As seen by this figure, the structure of a heart beat is defined by its P Q R S T components. The location, size, and shape of these components convey critical information about the physical operation of the heart. In the VPW-FRI model, the waveform may be modeled as a sum of Lorentzian (also known as Cauchy distribution) pulses, each of which includes a symmetric and an asymmetric component:

$$x(t) = \sum_{k=1}^{K} \frac{1}{\pi} \frac{c_k a_k + d_k (t - t_k)}{a_k^2 + (t - t_k)^2} \tag{1}$$

In this model, the waveform is considered to be formed from K pulses, each one denoted by an index k, and each one of which is defined by a center position $t_k$, a width or damping factor $a_k$, an amplitude for a symmetric pulse component $c_k$, and an amplitude for an asymmetric pulse component $d_k$. The number of Lorentzian pulses used to model a signal will depend on the nature of the signal. For an ECG waveform, using a K of five has been found generally suitable to reproduce the P, Q, R, S, and T features that are of clinical significance, although more robust results have been found in some cases if a six or seven pulse model is used, especially when the ECG waveforms being modeled have a relatively large amount of noise.

For some signal waveforms, the asymmetric amplitude $d_k$ can be set to zero, which reduces the number of parameters used to model the waveform. This is possible with the ECG waveforms, but the results in general are less accurate.

Figures 1, 1B:
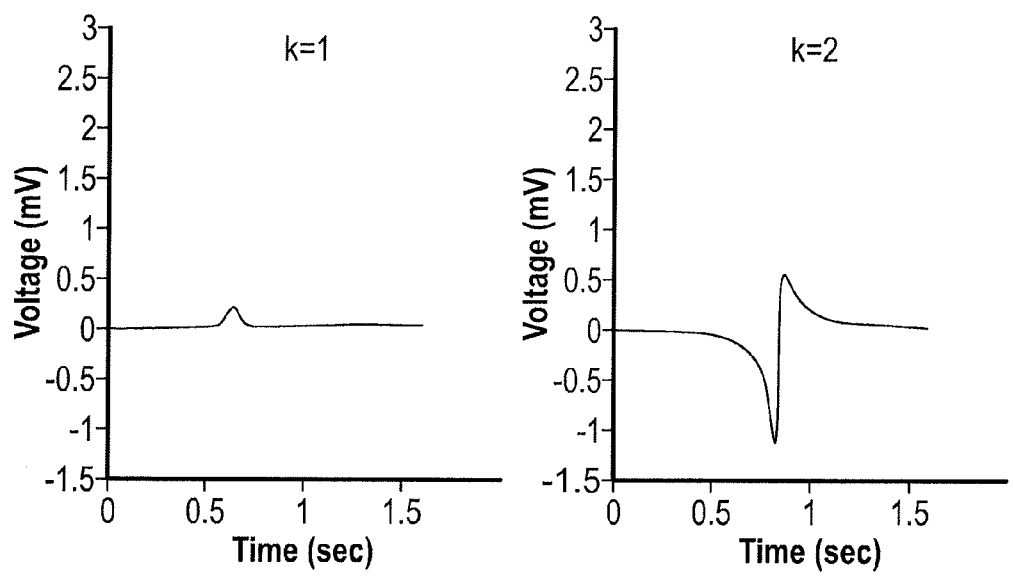

FIG. 1B illustrates five Lorentzian pulses of the form set forth in Equation 1 whose parameters were extracted from the original waveform of FIG. 1A using the methods described below. The sum of the pulses in FIG. 1B is shown in FIG. 1C. It can be seen that FIG. 1C is a good reproduction of the original signal of FIG. 1A. In this way, the signal from FIG. 1A is accurately parameterized by 20 parameters, four parameters (c, d, a, and t) for each of the five Lorentzian pulses of FIG. 1B and Equation 1.

As with other parameterization techniques, a method is required to derive the desired parameters from the original time domain data, which is typically a series of discrete waveform samples taken during the acquisition of an analog electrical signal output from electrodes coupled to a subject. The sampling rate may vary, but may be about 120-360 Hz, producing about 100-500 time domain samples of the waveform over the approximately 0.75 to 1.5 second time period of interest containing the P, Q, R, S, and T waveform features. It will be appreciated that parameterizing the waveform to 20 parameter values instead of the 100-500 original waveform sample values can produce a compression of the data by a factor of 5-25.

Although it may be possible to perform a derivation of the pulse parameters in the time domain (by, for example, using a regression analysis to find a, t, c, and d values for each of the five pulses that minimizes the differences between the values produced by Equation 1 at the sample times and the actual sample values), significant computational and accuracy advantages arise from performing the parameter derivation in the frequency domain.

Figures 1, 1B, 2:
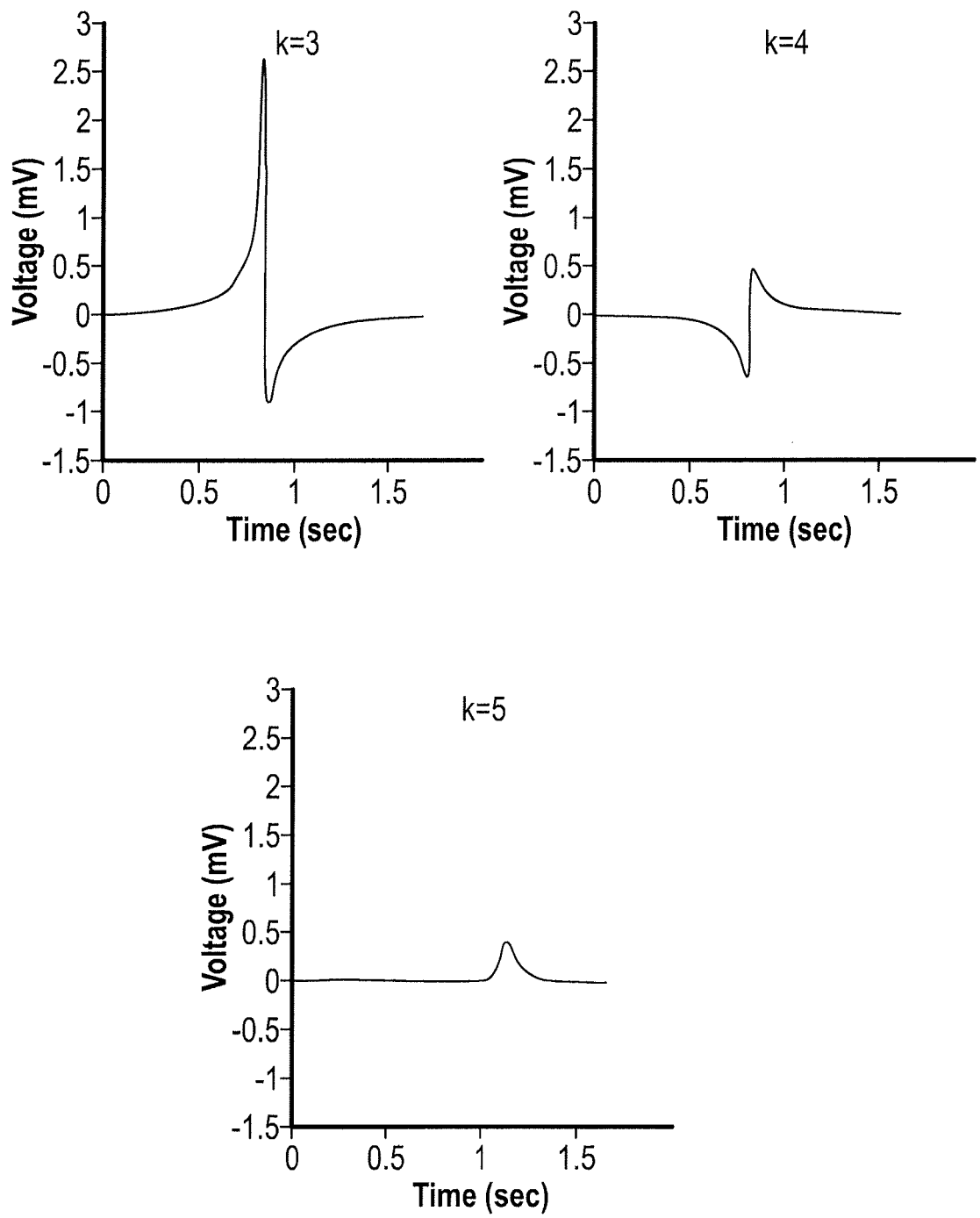
FIG. 2 is a flow chart of a method of parameterizing waveform containing variable width pulses.
Figure 1C:
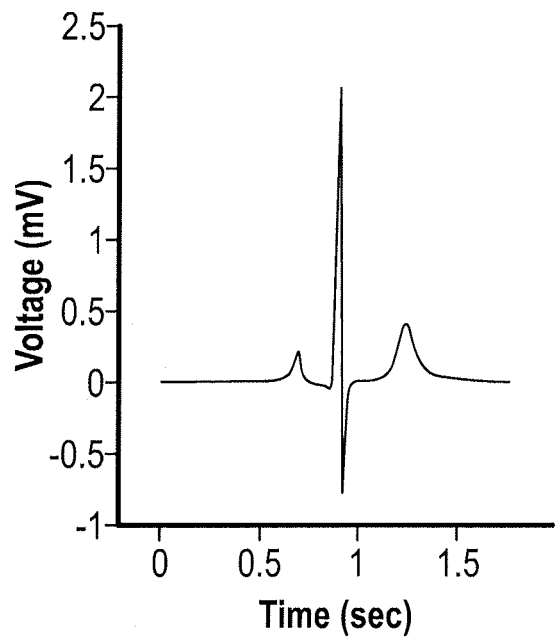
Figure 2:
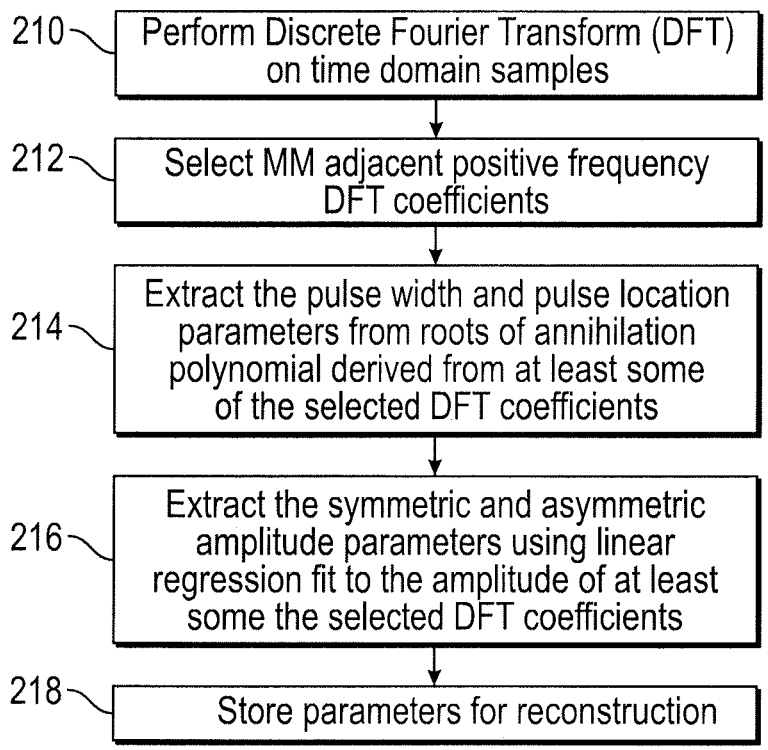
Figure 3:
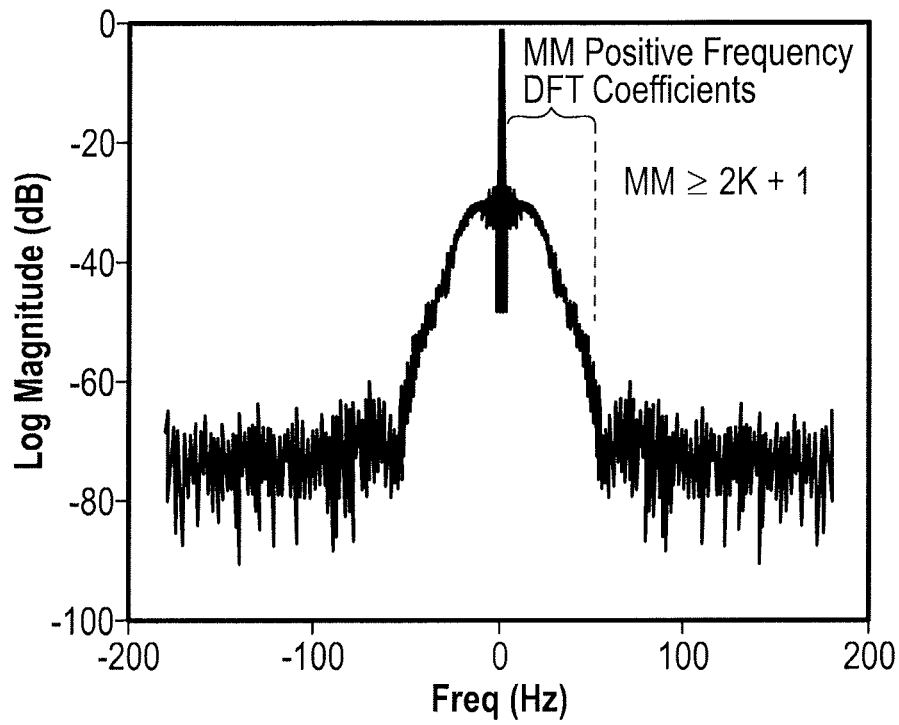
FIG. 3 is a graph of the spectrum of an ECG waveform.

FIG. 2 is a flow diagram of one method of signal analysis for deriving the VPW-FRI parameters in the frequency domain. In this implementation, the method starts at block 210, where a discrete Fourier transform (DFT) is performed on the original time domain samples. The method continues at block 212, where a set of MM positive frequency DFT coefficients are selected for further analysis to extract the above described pulse parameters. These steps are also illustrated graphically in FIG. 3, which shows an ECG frequency spectrum produced from a DFT algorithm applied to a time domain ECG waveform sampled at 360 Hz. As can be seen in FIG. 3, such a spectrum typically includes a region of decaying oscillations around 0 Hz and a transition region where the spectral energy decreases with increasing frequency to 60 or 70 Hz. A noise floor of around −70 dB can also be seen in FIG. 3 at frequencies above about 70 Hz. The details of the ECG waveform affect the frequencies and decay rate in the oscillating region, and the details of the shape of the transition region.

The set of MM DFT coefficients selected for analysis is on the positive side of 0 Hz, and includes at least 2K+1 adjacent DFT coefficient values. For the extraction method described in more detail below, positive frequency coefficients are selected because the set of coefficients cannot span across 0 Hz due to the methods used to perform the extraction as described further below. The extraction method described below also requires at least 2K+1 values as inputs, although stability and accuracy of results in the presence of noise is improved if more than this number are utilized. If K=5 (e.g. S pulse model) for an ECG waveform, it has been found useful for the number MM to be at least 25 or 30 DFT coefficients rather than the minimum of 11. The selected set of coefficients should include the oscillating region from near 0 Hz and extend to cover at least some of the transition region as well.

Referring back to FIG. 2, at block 214, the pulse width and pulse location parameters $a_k$ and $t_k$ are calculated from at least some of the selected DFT coefficients. To extract the damping factor (also referred to as the pulse width factor) $a_k$ and the time $t_k$ of each pulse, the method assumes that the DFT of block 210 was generated from a sampled time domain signal having the functional form of Equation 1. The DFT coefficients of a sampled sum of such Lorentzian pulses will follow the form of a sum of decaying sinusoids as shown in Equation 2:

$$\hat{X}(m) = \sum_{k=1}^{K} b_k e^{-(2\pi/\tau)a_k|m|-j(2\pi/\tau)t_k m} \quad (2)$$

$$\text{for } m = -\frac{N}{2} \ldots, 0, \ldots \frac{N}{2} - 1$$

where
$b_k = c_k - j d_k$ for positive m
$b_k = c_k + j d_k$ for negative m
$\tau = N/F_s$, where $F_s$ is the time domain sampling frequency and N is the number of time domain samples taken during the period of interest If the DFT of the original signal is assumed to be of the functional form of Equation 2, an annihilating filter can be constructed having roots related to the parameters $a_k$ and $t_k$. Techniques for solving this mathematical problem of deriving the parameters of a sampled (and possibly noisy) signal, where the signal is a sum of exponentially damped oscillations, have been developed and are well known. For example, spectral analysis techniques such as the Prony algorithm are known that can construct the annihilating polynomial and find its roots. Other spectral analysis techniques can also be used to find the roots of the annihilation polynomial such as ESPRIT. Such techniques have been used for similar purposes such as the Dirac-FRI methods mentioned above. Past attempts to use such methods, however, generally used DFT coefficients that include both positive and negative frequencies. When the pulses are assumed to have variable width, however, this presents a discontinuity, as can be seen from Equation 2, and the Prony algorithm, for example, does not model curves with exponential weights that change within the domain of analysis. One method of solving this problem is by recognizing that the spectrum of the time domain signal is conjugate symmetric, and it is not necessary that the coefficients used in the algorithm span 0 Hz. One can use only positive or only negative components of the spectrum (plus 0 Hz if desired) to satisfy the conditions of the Prony method. The complex roots of the annihilator polynomial in the spectral analysis will then provide the information to determine the damping factors in the model in addition to the pulse times. An additional advantage is gained by the recognition that frequency components supplied to the Prony method do not have to start at m=0. Since data obtained from real applications is often corrupted by DC offsets, it can be advantageous to avoid the m=0 term and, in some cases, the m=1 term in the analysis.

When one of the above described spectral analysis techniques is applied in this manner, this polynomial will have K roots which are (in polar form):

$$z_k = e^{-(2\pi/\tau)a_k} e^{j(2\pi/\tau)t_k} \quad k=1,\ldots K \quad (3)$$

It can be seen that the magnitude and phase of the roots are as follows:

$$|z_k| = e^{-(2\pi/\tau)a_k} \quad \angle z_k = \frac{2\pi}{\tau} t_k \qquad (4)$$

From these roots, the pulse locations $t_k$ can be computed:

$$t_k = (\tau/2\pi) \cdot \angle z_k \text{ for } k=1,\ldots,K \qquad (5)$$

where $t_k$ are the pulse locations in samples (0 to N−1) and the angle of $z_k$ is in radians (0 to $2\pi$).

The damping factors, $a_k$, are related to the magnitudes of the roots by the relation:

$$a_k = -(\tau/2\pi)\ln|z_k| \qquad (6)$$

After finding the damping factors and pulse times, at block 216 of FIG. 2 the symmetric and asymmetric amplitude parameters are extracted using a linear regression fit of DFT coefficients to be generated by Equation 2 to the DFT coefficients generated from the original time domain signal at block 210.

To accomplish this, a set of linear equations may be defined by matching a set of L values of X(m) from the input data with values expressed by the model in Equation 2. This set may be some or all of the MM previously selected coefficients, or any other selection of L values for m≥0. A minimum of K signal values and K equations (L≥K) are needed to form a matrix equation which may be inverted (or least squares inverted) to obtain the values of $b_k$. In practice, more signal values are generally used and the values of $b_k$ are determined by a least squares method.

The above set of linear equations can be described as follows:

$$\hat{X}\{m\} = \sum_{k=1}^{K} b_k e^{-(2\pi/\tau)a_k m - j(2\pi/\tau)t_k m} = \sum_{k=1}^{K} b_k z_k^{-m} \quad m \geq 0 \qquad (7a)$$

where:

$$z_k = e^{(2\pi/\tau)a_k + j(2\pi/\tau)t_k}, b_k = c_k - jd_k$$

Defining:

$$G = [z_k^{-m}] (L \times K \text{ matrix}) \qquad (7b)$$

$$b = [b_k] (K \times 1 \text{ column vector}) \qquad (7c)$$

$$x = [X\{m\}] (L \times 1 \text{ column vector}) \, m = \{\text{set of } L \text{ freq samples}\} \qquad (7d)$$

The solution for c can be expressed as:

$$Gb = x \qquad (7e)$$

$$b = \text{inv}(G)x \qquad (7f)$$

where inv(G) is the least squares (Moore-Penrose) pseudo-inverse of the matrix G.

When the components of the column vector [b] are determined with this method, the real part of each $b_k$ is the symmetric amplitude $c_k$ of pulse k, and the imaginary part of each $b_k$ is the asymmetric amplitude $d_k$ of pulse k.

After all the parameters $a_k$, $t_k$, $c_k$, and $d_k$ are calculated, the parameters are stored at block 218 for future signal reconstruction. When this model is applied, the complete waveform can be compressed to four values for each pulse (plus potentially an additional DC shift parameter), which for a five pulse waveform is only twenty or twenty-one values, much less than the number of time domain (or frequency domain) values that would be stored as representative of the waveform if a conventional Nyquist rate sampling method were used.

Figure 4:
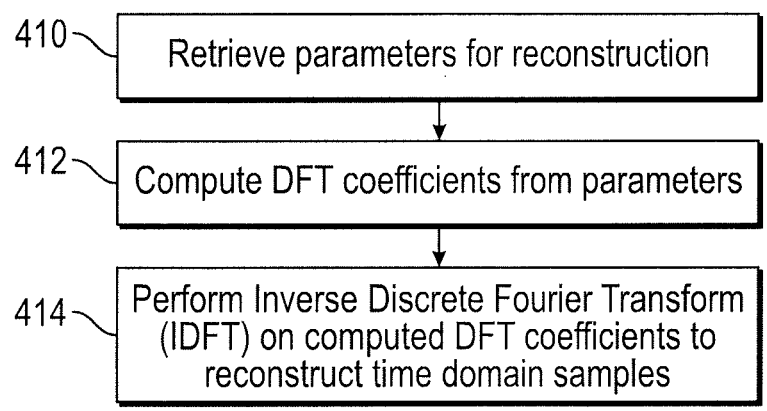
FIG. 4 is a flowchart of a method of signal reconstruction using the parameters generated with the method of FIG. 2.

FIG. 4 is a flow diagram of signal reconstruction from the stored parameters. In this implementation, the stored parameters $a_k$, $t_k$, $c_k$, and $d_k$ are retrieved at block 410. From the stored parameters, at block 412 DFT coefficients for positive m frequency indices are computed using Equation 2 and the retrieved parameters. Coefficients for negative m frequency indices may be computed by taking the complex conjugates of the positive m values produced by Equation 2. At block 414, an inverse discrete Fourier transform (IDFT) is performed on the DFT coefficients, producing a set of time domain values that represent the original time domain signal. It will be appreciated that an alternative reconstruction method may be used in the time domain, where the parameters $a_k$, $t_k$, $c_k$, and $d_k$ are plugged into Equation 1 to directly produce time domain data. Care should be taken in this case to use a shifted periodic version of Equation 1 if the original signal has any significant DC offset. This complication is not present if the frequency domain reconstruction of FIG. 4 is utilized.

Figure 5:
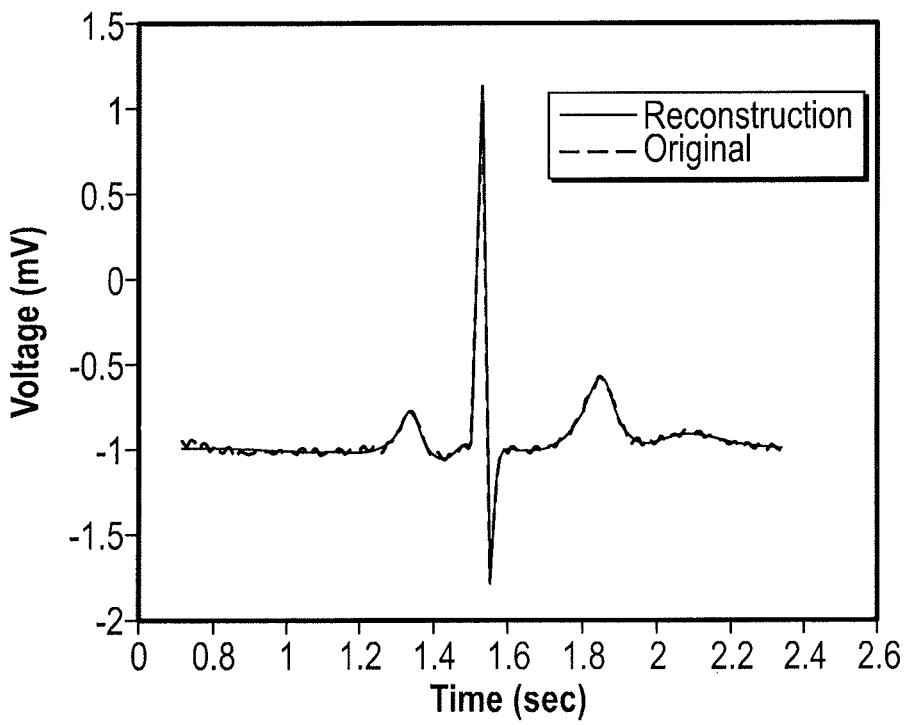
FIG. 5 is a graph comparing an original time domain signal with a reconstruction of the signal using VPW-FRI parameters.
Figure 6:
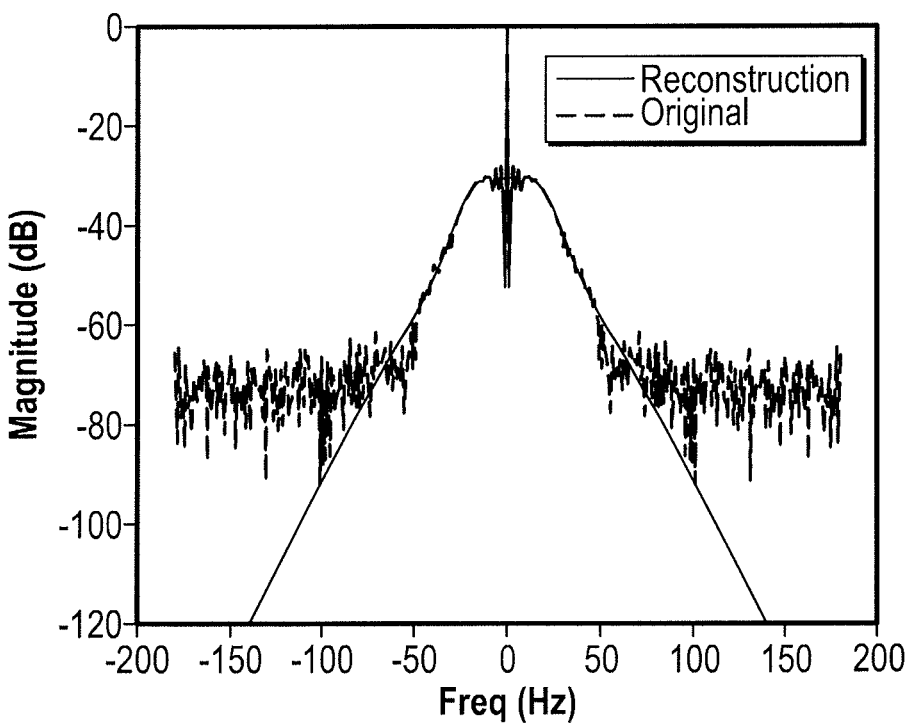
FIG. 6 is a graph comparing the time domain waveforms of FIG. 5 in the frequency domain.

To illustrate the utility of this approach, the VPW-FRI model and the analysis method defined by this disclosure, FIGS. 5 and 6 show the results of the analysis of a real heart beat waveform obtained from the MIT/BIH data base. In FIG. 5, the original time domain data is shown in dashed line, and the reconstruction output from the above described method (at block 414 of FIG. 4 for example) is shown in solid line. In FIG. 6, the DFT of the original signal (originally sampled at 360 Hz) is shown in dashed line, and the DFT coefficients produced by the method using Equation 2 at block 412 of FIG. 4 are shown in solid line.

Figure 7A:
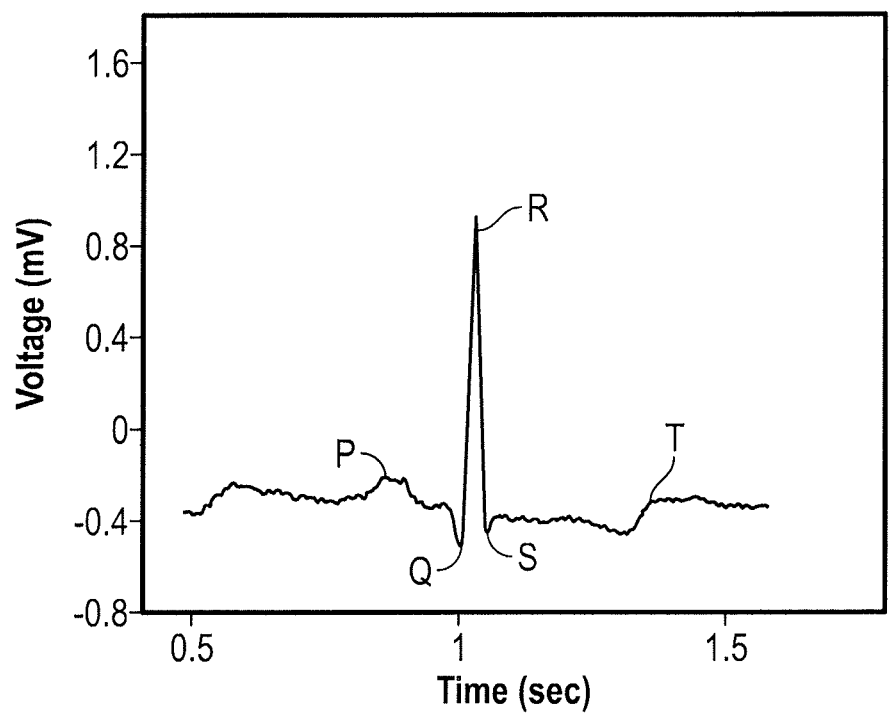
FIGS. 7A and 7B illustrate an original time domain ECG waveform and a reconstruction of the waveform using downsampled data.
Figure 7B:
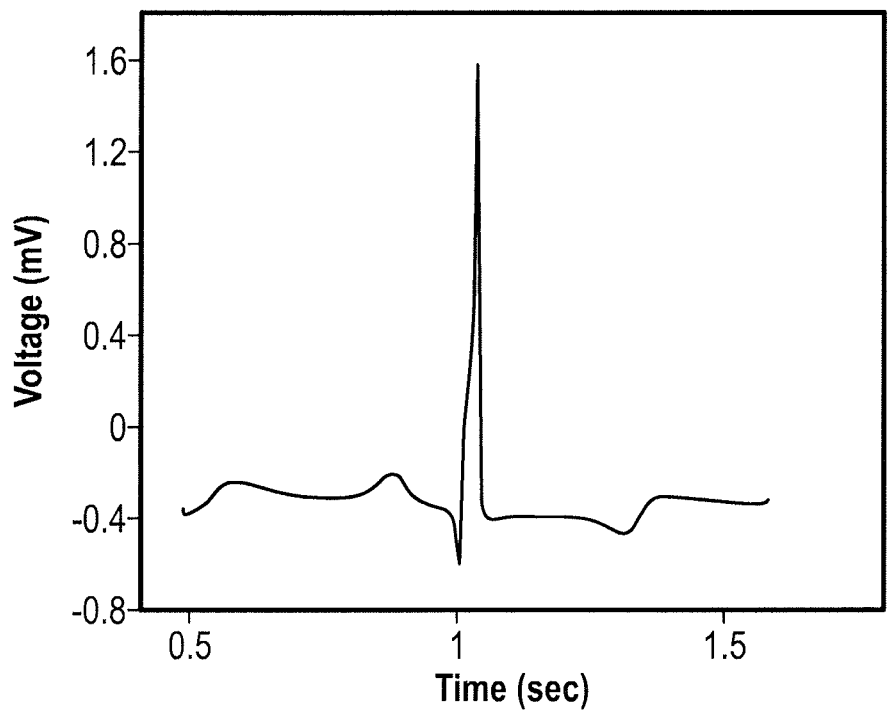

The above method of signal processing works very well for ECG waveforms that are sampled at relatively high rates such as 120 Hz or more. In practice, however, stored time domain samples often have lower frequency, sometimes being down-sampled to 60 Hz, for example. When lower frequency sampled data is used, the VPW-FRI algorithm may not accurately reproduce all of the important features of the waveform. This is illustrated in FIGS. 7A and 7B, which illustrate an original 360 Hz sampled ECG waveform and a VPW-FRI reconstruction of the waveform of FIG. 7A when the input data is not the 360 Hz original data, but is a decimated data set with a 60 Hz sample frequency instead where only one original sample in six is used for analysis and reconstruction. As can be seen in FIG. 7B, the R peak has a strong overshoot in amplitude, and the small S peak in FIG. 7A is essentially absent in FIG. 7B.

Figure 8:
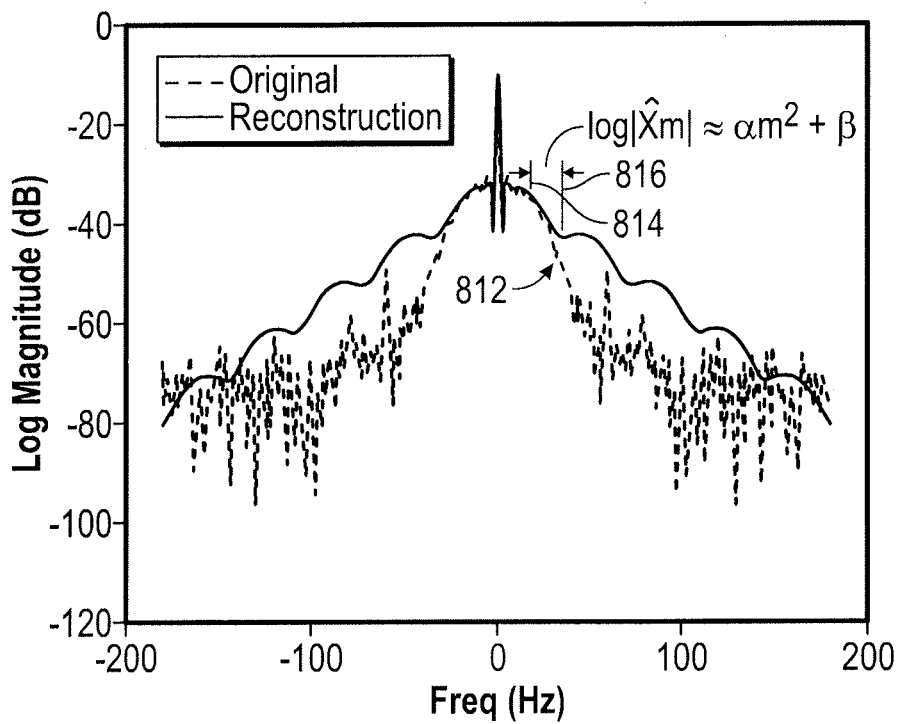
FIG. 8 is a graph comparing the time domain waveforms of FIGS. 7A and 7B in the frequency domain.

FIG. 8 illustrates the difference between the original waveform of FIG. 7A and the reconstructed waveform of FIG. 7B in the frequency domain. In FIG. 8, the dashed line illustrates the DFT of the original 360 Hz sampled waveform. The solid line illustrates the DFT coefficients produced by Equation 2 at, for example, block 412 of FIG. 4 following extraction of the VPW-FRI parameters from the 60 Hz sample set. The deviation between the actual spectrum and the reconstructed spectrum becomes large above about 30 Hz (which corresponds to the sampling frequency of 60 Hz). In general, for frequencies from 30 to 100 Hz, the reconstruction overestimates the amplitudes. This produces the overshoot and missed S peak seen in the time domain data of FIGS. 7A and 7B.

To improve signal reconstruction with downsampled original data, it has been observed that on a log scale, the amplitudes of the DFT coefficients of ECG waveforms tend to follow a parabolic functional form (on the log scale) in the transition region above about 10-15 Hz until the signal becomes basically noise at 60-100 Hz. This region is denoted 812 in FIG. 8. Although different ECG waveforms may have wider or narrower parabolic shapes in this area and may be shifted up or down, ECG waveforms in general exhibit this parabolic form.

This observation can be taken advantage of by adjusting the magnitudes of the DFT coefficients output by Equation 2 for m indices corresponding to frequencies higher than the input data sample frequency so that they follow the generally observed parabolic shape. To find the appropriate second order polynomial to use for the adjustment, the log of the reconstructed DFT data in the transition region corresponding to about 15 Hz to the input sample frequency is fit to a parameterized parabola of the form $\alpha m^2 + \beta$. This region extends from about line 814 to line 816 illustrated in FIG. 8. This is a region of the spectrum where the original DFT coefficients output from Equation 2 in the reconstruction process follow the DFT of the actual data well. Because the parabola is centered at 0 Hz, there is no need for a linear term, and the coefficient $\alpha$ will be negative, since the parabola opens downward. The parameters $\alpha$ and $\beta$ may be determined by finding $\alpha$ and $\beta$ values that minimize the difference between the DFT coefficient amplitudes produced by Equation 2 and the DFT coefficient amplitudes produced by the formula $\log X[m] = \alpha m^2 + \beta$ as shown in Equation 8, where X[m] are the DFT magnitudes produced by Equation 2 in the region between line 814 and 816 of FIG. 8:

$$\operatorname{argmin}\|\log X[m] - \alpha m^2 - \beta\|^2 \text{ over } \{\alpha, \beta\} \quad (8)$$

Once the parameters $\alpha$ and $\beta$ are determined, the magnitudes of the DFT coefficients produced by Equation 2 can be adjusted (without changing the phase) in the region above the sample frequency where the original DFT coefficients do not reproduce the spectrum well. Thus, for DFT coefficients corresponding to frequencies above the input sample frequency, the DFT coefficients can be modified in accordance with Equation 9:

$$\hat{X}[m] = \frac{\hat{X}[m]}{|X[m]|} e^{\alpha m^2 + \beta} \quad (9)$$

Figure 9:
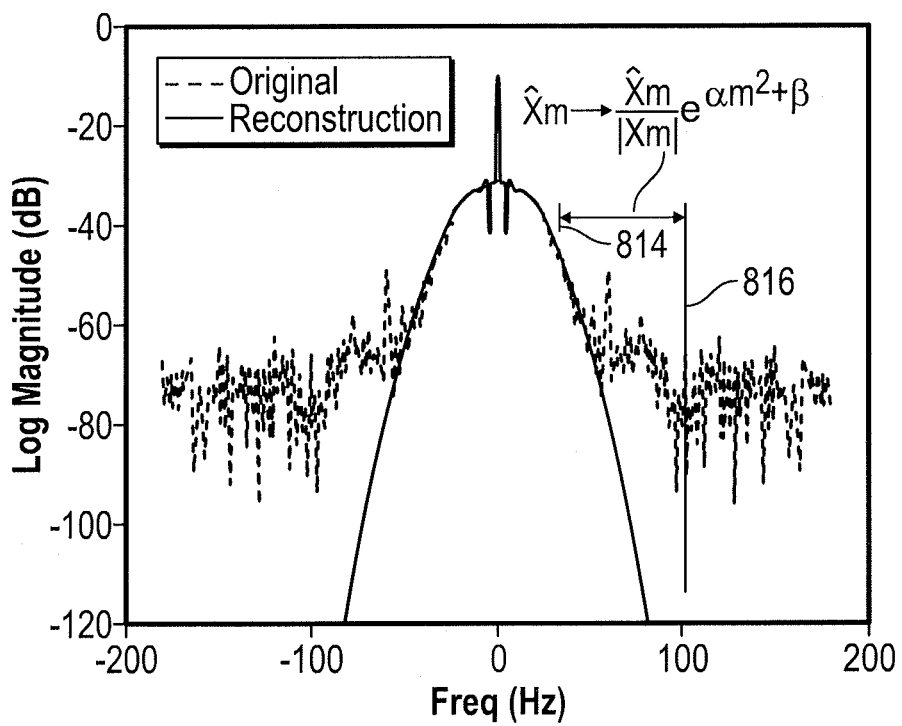
FIG. 9 is a graph comparing the frequency domain waveform of FIG. 7A with an adjusted frequency domain waveform used for reconstruction.
Figure 10A:
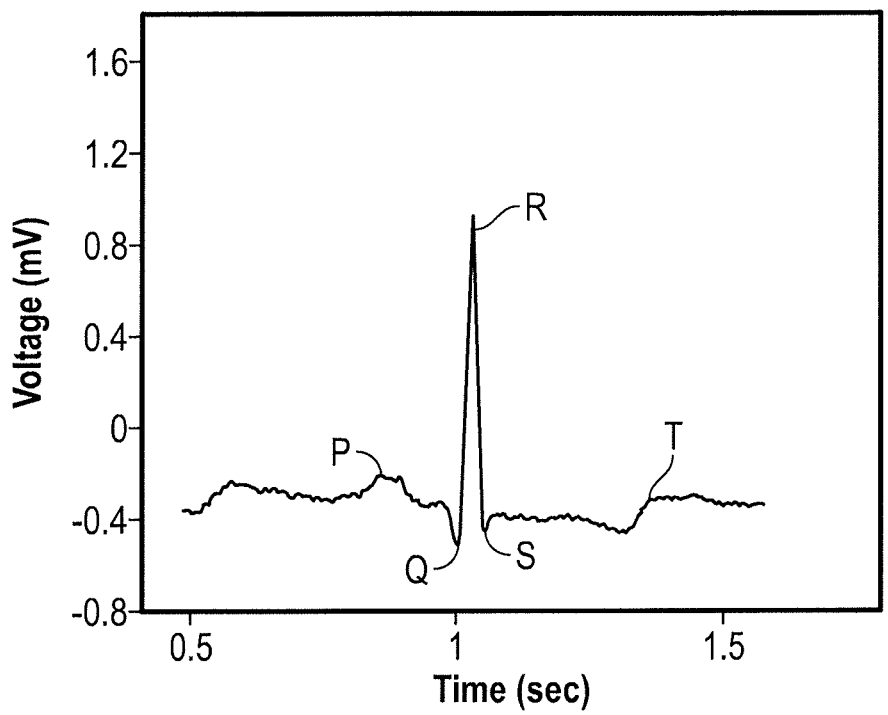
FIGS. 10A and 10B illustrate an original time domain ECG waveform and a reconstruction of the waveform using the adjusted frequency domain waveform of FIG. 9.
Figure 10B:
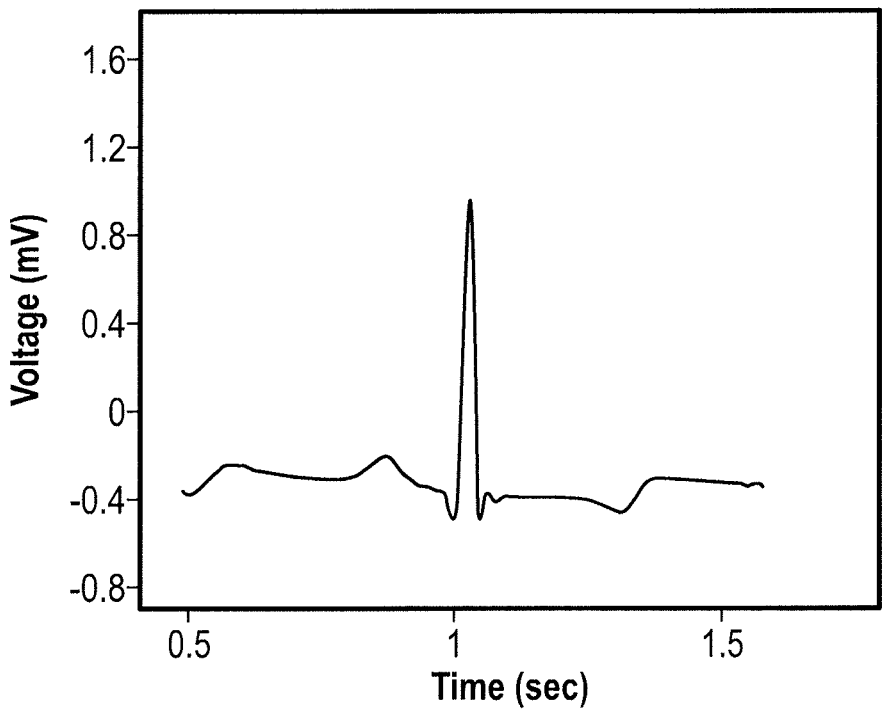

The result of this procedure is illustrated graphically in FIGS. 9 and 10. In FIG. 9, a set of DFT coefficients modified from the original outputs of Equation 2 is illustrated. The solid line of FIG. 9 is a graph of DFT coefficient output from Equation 2 for the region from 0 Hz up to about 30 Hz denoted by line 814. For the DFT coefficients from 30 Hz up to about 100 Hz (or beyond), denoted by line 1016, the DFT coefficients have an amplitude that is the DFT coefficients output from Equation 2 as modified according to Equation 9. The DFT now follows the parabolic shape defined between 15 Hz and 30 Hz all the way out to 100 Hz or more. In practice, the DFT coefficients past 60 to 80 Hz have little effect on the reconstruction. FIG. 10A shows the original time domain waveform sampled at 360 Hz, the same as is shown in FIG. 7A. FIG. 10B shows the time domain waveform produced by performing an IDFT on the solid line DFT of FIG. 9. With the correction from 30 Hz and upward, it can be seen in FIG. 10B that the overshoot of the R peak is removed, and the S peak is now reproduced.

Figure 11:
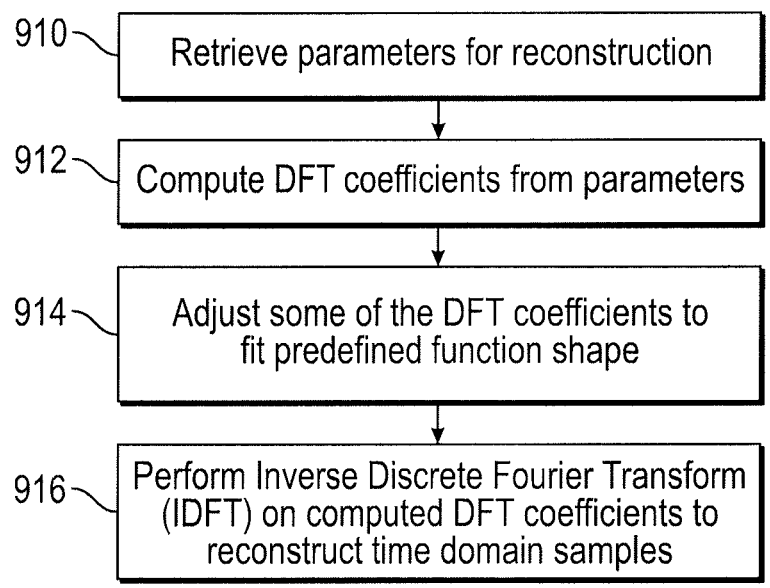
FIG. 11 is a flow chart of a method of signal reconstruction including DFT coefficient adjustment.

FIG. 11 is a flowchart illustrating this correction method. It generally follows the flow of FIG. 4, with the additional correction step described above. As also described above with reference to FIG. 4, the stored parameters $a_k$, $t_k$, $c_k$, and $d_k$ are retrieved at block 1110. From the stored parameters, at block 1112 DFT coefficients for positive m frequency indices are computed using Equation 2 and the retrieved parameters. Coefficients for negative m frequency indices may again be computed by taking the complex conjugates of the positive m values produced by Equation 2. At block 1114, some of the DFT coefficients are adjusted to fit a pre-defined function shape. For ECG waveforms, a parabolic functional shape has been found suitable. For other waveform sources, different functional shapes may be appropriate. At block 1116, an inverse discrete Fourier transform (IDFT) is performed on the DFT coefficients, producing a set of time domain values that represent the original time domain signal.

It will be appreciated that the $\alpha$ and $\beta$ parameters could be generated during the data analysis process described above with reference to FIG. 2. In this implementation, the parabolic curve fitting could be performed by generating the DFT coefficients from the extracted VPW-FRI parameters a, t, c, and d using Equation 2, generating a suitable $\alpha$ and $\beta$, and then storing these values along with the other VPW-FRI parameters. This eliminates the need to perform the parabolic curve fitting during reconstruction.

Figure 12A:
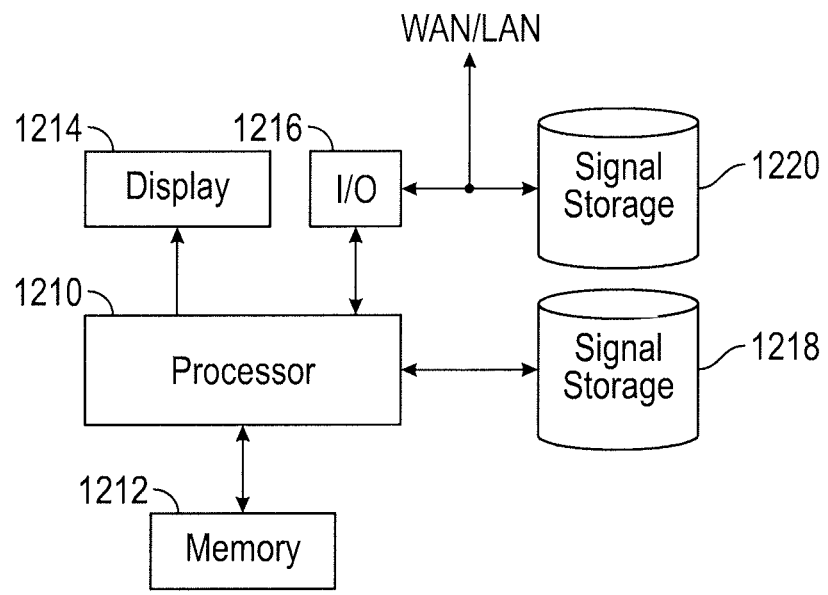
FIGS. 12A-12C illustrates embodiments of systems utilizing signal parameterization of the present disclosure.

The methods described above can be implemented in a wide variety of systems. FIG. 12A illustrates a block diagram of one device configured to implement the VPW-FRI methods. The device may include a processor 1210. The processor 1210 may also be referred to as a central processing unit (CPU). Memory 1212, which may include both read-only memory (ROM) and random access memory (RAM), provides instructions and data to the processor 1210. A portion of the memory 1212 may also include non-volatile random access memory (NVRAM). The processor 1210 typically performs logical and arithmetic operations based on program instructions stored within the memory 1212. The instructions in the memory 1212 may be executable to implement the methods of the VPW-FRI model described herein. For example, the instructions in the memory 1212 may be executable by the processor 1210 to implement the sequence of signal processing steps for the analysis and/or reconstruction of a waveform as shown in FIGS. 2, 4, and 11.

The processor 1210 may be configured to receive N samples (where N is a positive integer) of an input signal in the time domain from a local signal storage 1218 or a remote signal storage 1220. Further, the processor 1210 may transform the N samples utilizing a DFT algorithm to produce the transform coefficients X(m) in the frequency domain as described above. Alternatively, the signal storage may store DFT coefficients of original time domain signals, and these could be used as a starting point for the algorithm implemented by the processor 1210. A subset MM of the transform coefficients (whether received by or generated by the processor 1210), in particular a set of coefficients associated with positive frequencies, may be selected by the processor 1210. The subset MM of the transform coefficients may then be used by the processor to define the VPW-FRI parameters. These parameters may then be stored as compressed versions of the original data in signal storage 1218 or 1220. The original data can then be discarded or stored elsewhere. The processor may also be configured to retrieve VPW-FRI parameters from the signal storage memory 1218 or 1220. The processor may then generate DFT coefficients using the methods described above, and perform an IDFT on the generated DFT coefficients to reconstruct a time domain waveform. An output device such display 1214 or a printer may be used to display either original or reconstructed time domain data.

The signal storage memory 1218 and/or 1220 may comprise an ECG signal database. The processor may then use as input ECG signals, and store them as parameters computed utilizing the VPW-FRI algorithm. Storage of the ECG signals as such parameters may reduce the memory allocation necessary for storing such ECG signals. The system of FIG. 12A may be employed, for example, at a hospital to efficiently store ECG signals as part of patient medical history records.

Although a number of separate components are illustrated in FIG. 12A, those of skill in the art will recognize that one or more of the components may be combined or commonly implemented. Further, each of the components illustrated in FIG. 12A may be implemented using a plurality of separate elements.

Figure 12B:
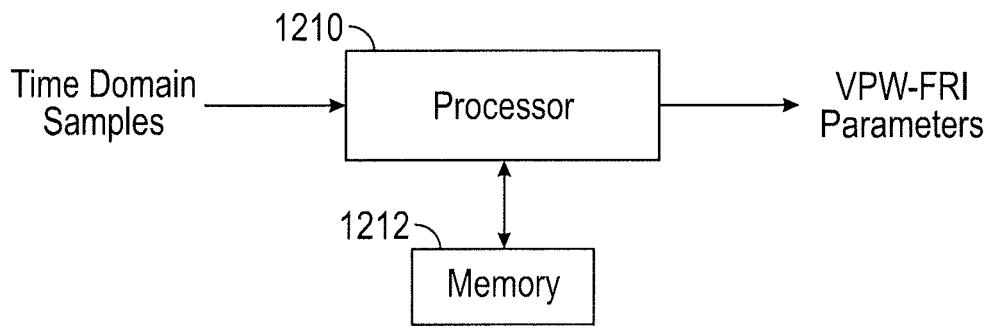
Figure 12C:
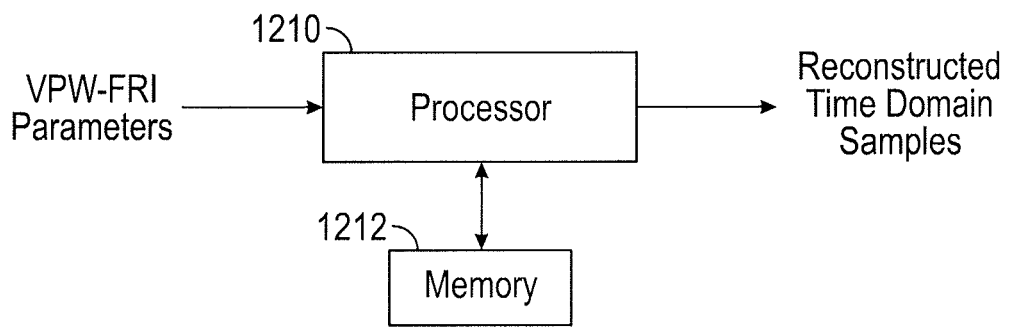

FIGS. 12B and 12C are block diagrams illustrating that different processors 1210 which may be geographically separated can separately perform the signal analysis and signal reconstruction. In FIG. 12B, the processor 1210 is dedicated to performing the signal analysis portion of the process. This processor takes time domain samples and produces VPW-FRI parameters. In FIG. 12C, the processor is dedicated to reconstruction. This processor takes VPW-FRI parameters as an input, and produces reconstructed time domain samples as an output.

Figure 13:
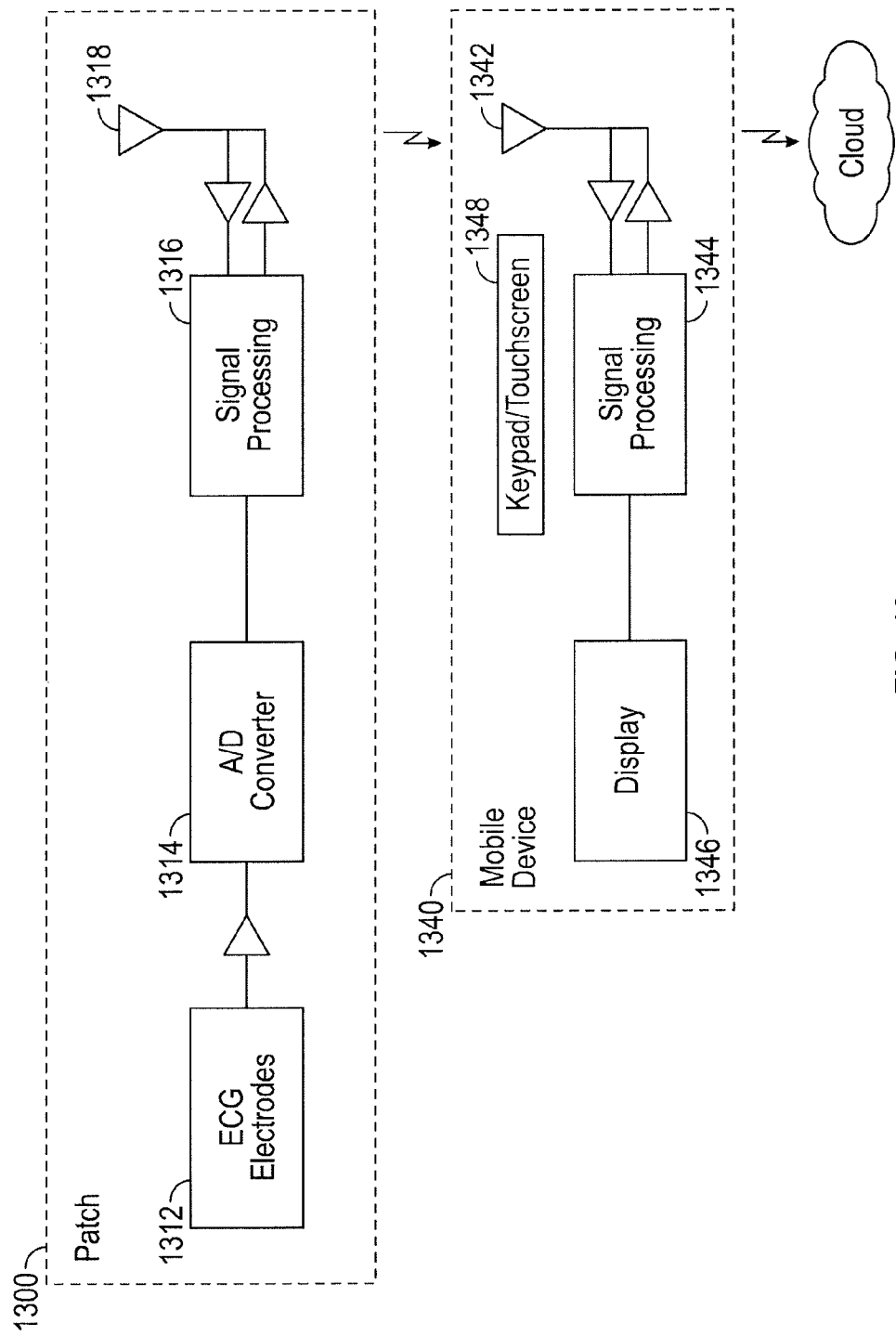
FIG. 13 illustrates an embodiment of a system utilizing signal parameterization of the present disclosure.

FIG. 13 illustrates another system in which the above described methods can be implemented. In this system, a patch ECG monitor 1300 incorporates ECG electrodes 1312 and is mounted with adhesive for example on a subject as an ambulatory cardiac monitoring device. The signal from the electrodes is routed to an A/D converter 1314 which produces time domain samples of the signal. These samples are sent to signal processing circuitry 1316 which may be configured to produce the VPW-FRI parameters of pulse width, time, and symmetric and asymmetric amplitude described above. These may be sent wirelessly via antenna 1318 to a mobile device 1340 such as a cell phone, tablet, or other portable electronic system, which receives the parameters via antenna 1342 and routes the parameters to signal processing circuitry 1344 in the mobile device 1340. As noted above, the signal processing circuitry may also produce the $\alpha$ and $\beta$ parameters and send them to the mobile device for curve fitting during reconstruction described above. It will be appreciated that the components of the patch 1300 need not be mounted together on the same physical substrate, but could be split up in a variety of ways.

The signal processing circuitry 1344 in the mobile device 1340 may be configured to reconstruct the ECG waveforms using the VPW-FRI parameters and the $\alpha$ and $\beta$ parameters that are computed on the mobile device 1340 or are received from the patch monitor 1300. The reconstructed signal may be displayed on a display 1346 and manipulated with a keypad/touchscreen 1348 on the mobile device. The mobile device may also be configured to transmit either the reconstructed waveform and/or the parameters to an external network such as the Internet for storage, review by a physician, etc.

Because the on-body mounted system 1300 should use as little power as possible, it is advantageous to minimize the sampling rate of the A/D converter and also minimize the amount of data that must be transmitted from the on-body system 1300 to the mobile device 1340. The compression and accurate reconstruction provided by the methods described above can reduce the power consumed by the on-body system 1300.

The various illustrative logic, logical blocks, modules, and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. In some implementations, particular steps and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A computer implemented method of reconstructing a time domain waveform from a compressed original time domain waveform comprising:
   receiving, in a processor, parameters defining a compressed form of the original time domain waveform;
   generating, with the processor, discrete Fourier transform (DFT) coefficients from the parameters;
   adjusting without zeroing, with the processor, the amplitudes of at least some of the generated DFT coefficients to more closely fit the amplitudes of the at least some of the generated DFT coefficients to a predefined functional shape; and
   performing, with the processor, an inverse discrete Fourier transform (IDFT) on a set of DFT coefficients including the adjusted DFT coefficients to produce a reconstructed time domain waveform,
   wherein the original time domain waveform is an electrocardiogram (ECG) signal collected from ECG electrodes and the predefined functional shape is determined based at least in part on the ECG signal.

2. The method of claim 1, wherein the predefined functional shape is parabolic on a logarithmic scale.

3. The method of claim 1, further comprising deriving the parameters and storing the parameters for reconstruction.

4. The method of claim 1, wherein the parameters are derived from time domain samples of the original time domain waveform.

5. The method of claim 4, wherein the time domain samples are spaced at less than 120 Hz.

6. The method of claim 4, wherein the parameters represent characteristics of each of a series of pulses that model the original time domain waveform, and wherein the characteristics include at least a peak position, a peak amplitude, and a pulse width.

7. The method of claim 4, wherein the parameters are derived by a method comprising:
   obtaining, by at least one processor, a series of at least MM discrete Fourier transform coefficients of an N sample time domain ECG signal, where MM is greater than 2K;
   determining, by the at least one processor, K roots of an annihilator polynomial using the MM discrete Fourier transform coefficients;
   based at least in part on the determined roots, deriving, by the at least one processor, a location and width of K pulses; and
   deriving, by the at least one processor, one or both of a symmetric and asymmetric amplitude for each of the K pulses.

8. The method of claim 2, wherein the parameters are derived by a method comprising:
   obtaining, by at least one processor, a series of at least MM discrete Fourier transform coefficients of an N sample time domain signal, where MM is greater than 2K;
   determining, by the at least one processor, K roots of an annihilator polynomial using the MM discrete Fourier transform coefficients;
   based at least in part on the determined roots, deriving, by the at least one processor, a location and width of K pulses; and
   deriving, by the at least one processor, one or both of a symmetric and asymmetric amplitude for each of the K pulses.

9. The method of claim 1, wherein the adjusting comprises transforming a first set of generated DFT coefficients according to the formula:
   adjusted $$\hat{X}[m] = \frac{\hat{X}[m]}{|X[m]|} e^{\alpha m^2 + \beta}$$

wherein $\alpha$ and $\beta$ are parameters characterizing the predefined functional shape.

10. The method of claim 9, wherein $\alpha$ and $\beta$ are derived by minimizing the formula:

$$\|\log X[m] - \alpha m^2 - \beta\|^2 \text{ over } \{\alpha, \beta\}$$

using a second set of generated DFT coefficients different from the first set.

11. The method of claim 2, wherein the adjusting comprises transforming a first set of generated DFT coefficients according to the formula:
adjusted $$\hat{X}[m] = \frac{\hat{X}[m]}{|X[m]|} e^{\alpha m^2 + \beta}$$

wherein $\alpha$ and $\beta$ are parameters characterizing the predefined functional shape.

12. The method of claim 11, wherein $\alpha$ and $\beta$ are derived by minimizing the formula:

$$\|\log X[m] - \alpha m^2 - \beta\|^2 \text{ over } \{\alpha, \beta\}$$

using a second set of generated DFT coefficients different from the first set.

13. The method of claim 12, wherein the parameters are derived by a method comprising:
obtaining, by at least one processor, a series of at least MM discrete Fourier transform coefficients of an N sample time domain ECG signal, where MM is greater than 2K;
determining, by the at least one processor, K roots of an annihilator polynomial using the MM discrete Fourier transform coefficients;
based at least in part on the determined roots, deriving, by the at least one processor, a location and width of K pulses; and
deriving, by the at least one processor, one or both of a symmetric and asymmetric amplitude for each of the K pulses.

14. A processing apparatus comprising:
a memory having stored therein parameters defining a compressed form of an original time domain waveform;
a processor configured to:
retrieve the parameters;
generate discrete Fourier transform (DFT) coefficients from the parameters;
adjust without zeroing the amplitudes of at least some of the generated DFT coefficients to more closely fit the amplitudes of the at least some of the generated DFT coefficients to a predefined functional shape; and
perform an inverse discrete Fourier transform (IDFT) on a set of DFT coefficients including the adjusted DFT coefficients to produce a reconstructed time domain waveform,
wherein the original time domain waveform is an electrocardiogram (ECG) signal collected from ECG electrodes and the predefined functional shape is determined based at least in part on the ECG signal.

15. The apparatus of claim 14, wherein the predefined functional shape is parabolic on a logarithmic scale.

16. The apparatus of claim 14, wherein the processor is configured to derive the parameters and store the parameters in the memory.

17. The apparatus of claim 16, wherein the parameters are derived from time domain samples of the original time domain waveform.

18. The apparatus of claim 17, wherein the time domain samples are spaced at less than 120 Hz.

19. The apparatus of claim 17, wherein the parameters represent characteristics of each of a series of pulses that model the original time domain waveform, and wherein the characteristics include at least a peak position, a peak amplitude, and a pulse width.

20. The apparatus of claim 17, wherein the processor is configured to derive the parameters by a method comprising:
obtaining a series of at least MM discrete Fourier transform coefficients of an N sample time domain ECG signal, where MM is greater than 2K;
determining K roots of an annihilator polynomial using the MM discrete Fourier transform coefficients;
based at least in part on the determined roots, deriving a location and width of K pulses; and
deriving one or both of a symmetric and asymmetric amplitude for each of the K pulses.

21. The apparatus of claim 15, wherein the processor is configured to derive the parameters by a method comprising:
obtaining a series of at least MM discrete Fourier transform coefficients of an N sample time domain signal, where MM is greater than 2K;
determining K roots of an annihilator polynomial using the MM discrete Fourier transform coefficients;
based at least in part on the determined roots, deriving a location and width of K pulses; and
deriving, by the at least one processor, one or both of a symmetric and asymmetric amplitude for each of the K pulses.

22. The apparatus of claim 14, wherein the adjusting comprises transforming a first set of generated DFT coefficients according to the formula:
adjusted $$\hat{X}[m] = \frac{\hat{X}[m]}{|X[m]|} e^{\alpha m^2 + \beta}$$

wherein $\alpha$ and $\beta$ are parameters characterizing the predefined functional shape.

23. The apparatus of claim 22, wherein $\alpha$ and $\beta$ are derived by minimizing the formula:

$$\|\log X[m] - \alpha m^2 - \beta\|^2 \text{ over } \{\alpha, \beta\}$$

using a second set of generated DFT coefficients different from the first set.

24. The apparatus of claim 15, wherein the adjusting comprises transforming a first set of generated DFT coefficients according to the formula:
adjusted $$\hat{X}[m] = \frac{\hat{X}[m]}{|X[m]|} e^{\alpha m^2 + \beta}$$

wherein $\alpha$ and $\beta$ are parameters characterizing the predefined functional shape.

25. The apparatus of claim 24, wherein $\alpha$ and $\beta$ are derived by minimizing the formula:

$$\|\log X[m] - \alpha m^2 - \beta\|^2 \text{ over } \{\alpha, \beta\}$$

using a second set of generated DFT coefficients different from the first set.

26. The apparatus of claim 25, wherein the processor is configured to derive the parameters by a method comprising:
obtaining a series of at least MM discrete Fourier transform coefficients of an N sample time domain ECG signal, where MM is greater than 2K;
determining K roots of an annihilator polynomial using the MM discrete Fourier transform coefficients;
based at least in part on the determined roots, deriving a location and width of K pulses; and deriving one or both of a symmetric and asymmetric amplitude for each of the K pulses.

27. The apparatus of claim 14, further comprising an antenna coupled to the processor, and wherein the processor is configured to receive the parameters wirelessly with the antenna and store the parameters in the memory.

28. The apparatus of claim 27, additionally comprising a body mountable device, the body mountable device comprising:
ECG electrodes;
an analog to digital converter;
a second antenna; and
a second processor, wherein the second processor is configured to receive time domain samples of signals generated by the ECG electrodes, derive the parameters from the time domain samples, and transmit the parameters with the second antenna.

29. The apparatus of claim 28, wherein the second processor is configured to derive the parameters by a method comprising:
obtaining a series of at least MM discrete Fourier transform coefficients of an N sample time domain signal, where MM is greater than 2K;
determining K roots of an annihilator polynomial using the MM discrete Fourier transform coefficients;
based at least in part on the determined roots, deriving a location and width of K pulses; and
deriving one or both of a symmetric and asymmetric amplitude for each of the K pulses.

30. A non-transitory, computer readable medium comprising instructions that when executed cause a processor to perform a method comprising:
receiving, in the processor, parameters defining a compressed form of an original time domain waveform;
generating, with the processor, discrete Fourier transform (DFT) coefficients from the parameters;
adjusting without zeroing, with the processor, the amplitudes of at least some of the generated DFT coefficients to more closely fit the amplitudes of the at least some of the generated DFT coefficients to a predefined functional shape;
performing, with the processor, an inverse discrete Fourier transform (IDFT) on a set of DFT coefficients including the adjusted DFT coefficients to produce a reconstructed time domain waveform,
wherein the original time domain waveform is an electrocardiogram (ECG) signal collected from ECG electrodes and the predefined functional shape is determined based at least in part on the ECG signal.

31. The medium of claim 30, wherein the method further comprises deriving the parameters and storing the parameters for reconstruction.

32. The medium of claim 31, wherein deriving the parameters comprises:
obtaining a series of at least MM discrete Fourier transform coefficients of an N sample time domain ECG signal, where MM is greater than 2K;
determining K roots of an annihilator polynomial using the MM discrete Fourier transform coefficients;
based at least in part on the determined roots, deriving a location and width of K pulses; and
deriving one or both of a symmetric and asymmetric amplitude for each of the K pulses.

33. The medium of claim 30, wherein the adjusting comprises transforming a first set of generated DFT coefficients according to the formula:
adjusted $$\hat{\hat{X}}[m] = \frac{\hat{X}[m]}{|X[m]|} e^{\alpha m^2 + \beta}$$

wherein $\alpha$ and $\beta$ are parameters characterizing the predefined functional shape.

34. The medium of claim 33, wherein $\alpha$ and $\beta$ are derived by minimizing the formula:

$\|\log X[m] - \alpha m^2 - \beta\|^2$ over $\{\alpha, \beta\}$ using a second set of generated DFT coefficients different from the first set.

* * * * *